(12) United States Patent
Gong et al.

(10) Patent No.: US 12,204,057 B2
(45) Date of Patent: Jan. 21, 2025

(54) SYSTEMS AND METHODS FOR ULTRASOUND ATTENUATION COEFFICIENT ESTIMATION

(71) Applicant: Mayo Foundation for Medical Education and Research, Rochester, MN (US)

(72) Inventors: Ping Gong, Rochester, MN (US); Pengfei Song, Champaign, IL (US); Shigao Chen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 470 days.

(21) Appl. No.: 17/420,641

(22) PCT Filed: Jan. 6, 2020

(86) PCT No.: PCT/US2020/012325
§ 371 (c)(1),
(2) Date: Jul. 2, 2021

(87) PCT Pub. No.: WO2020/142760
PCT Pub. Date: Jul. 9, 2020

(65) Prior Publication Data
US 2022/0091243 A1    Mar. 24, 2022

Related U.S. Application Data

(60) Provisional application No. 62/788,430, filed on Jan. 4, 2019.

(51) Int. Cl.
*G01S 7/52* (2006.01)
*A61B 8/08* (2006.01)
*G01N 29/11* (2006.01)

(52) U.S. Cl.
CPC ............ *G01S 7/52036* (2013.01); *A61B 8/08* (2013.01); *A61B 8/48* (2013.01); *A61B 8/5223* (2013.01);
(Continued)

(58) Field of Classification Search
CPC .......... G01N 29/11; G01N 2291/02466; G01S 7/52028; G01S 7/52036; G01S 7/52077; A61B 8/5223; A61B 8/48; A61B 8/08
See application file for complete search history.

(56) References Cited

U.S. PATENT DOCUMENTS 6,419,632 B1 * 7/2002 Shiki ................... G01S 15/8979
600/443
11,166,699 B2   11/2021 Labyed et al.
(Continued)

FOREIGN PATENT DOCUMENTS

CN      101766497 A      7/2010
CN      102608212 A      7/2012
(Continued)

OTHER PUBLICATIONS

Kim, H. et al. "Estimation of ultrasound attenuation from broadband echo-signals using bandpass filtering." ieee transactions on ultrasonics, ferroelectrics, and frequency control 55.5 (2008): 1153-1159.
(Continued)

*Primary Examiner* — Katherine L Fernandez
*Assistant Examiner* — Brooke Lyn Klein
(74) *Attorney, Agent, or Firm* — Quarles & Brady LLP (57) ABSTRACT

Described here are systems and methods for improved ultrasound attenuation coefficient estimation ("ACE") techniques. In one aspect, noise can be suppressed by using signal-to-noise ratio ("SNR") as a quality control metric for restricting depth ranges for ACE. In this way, the proper
(Continued)

depth range for each frequency component can be adaptively changed with sufficient SNR for ACE. In another aspect, elevation focusing normalization is used to reduce errors associated with diffraction effects when estimating attenuation coefficient. In another aspect, methods for suppressing noise in ACE techniques is provided. Noise can be suppressed based on a noise field computed from measurements obtained without ultrasound transmission, based on a unique combination of consecutive image frames, based on singular value decomposition ("SVD") clutter filtering cutoff values, or combinations thereof.

10 Claims, 6 Drawing Sheets

(52) U.S. Cl.
CPC .......... *G01N 29/11* (2013.01); *G01S 7/52028* (2013.01); *G01S 7/52077* (2013.01); *G01N 2291/02466* (2013.01)

(56) References Cited

U.S. PATENT DOCUMENTS

| | | | | |
|---|---|---|---|---|
| 2010/0240992 | A1* | 9/2010 | Hao | G01S 7/5205 |
| | | | | 600/437 |
| 2013/0165785 | A1* | 6/2013 | Lause | A61B 8/5276 |
| | | | | 600/443 |
| 2014/0316292 | A1* | 10/2014 | McRae | G16H 40/63 |
| | | | | 600/504 |
| 2016/0331352 | A1* | 11/2016 | Kawashima | A61B 8/5269 |
| 2017/0150948 | A1* | 6/2017 | Kanayama | A61B 8/488 |
| 2018/0143166 | A1* | 5/2018 | Feleppa | G01N 29/449 |
| 2018/0220997 | A1 | 8/2018 | Song | |
| 2018/0284251 | A1 | 10/2018 | Labyed et al. | |
| 2020/0146656 | A1 | 5/2020 | Gong | |

FOREIGN PATENT DOCUMENTS

| | | |
|---|---|---|
| CN | 104997534 A | 10/2015 |
| WO | 2017146886 A1 | 8/2017 |
| WO | 2018237244 A1 | 12/2018 |

OTHER PUBLICATIONS

Omari, E. A., et al. "Signal to noise ratio comparisons for ultrasound attenuation slope estimation algorithms." Medical physics 41.3 (2014): 032902.

Samimi, K. et al. "Ultrasonic attenuation imaging using spectral cross-correlation and the reference phantom method." 2011 IEEE International Ultrasonics Symposium. IEEE, 2011.

International Searching Authority. International Search Report and Written Opinion for application PCT/US2020/012325. Mailed on Jun. 23, 2020. 15 pages.

* cited by examiner

SYSTEMS AND METHODS FOR ULTRASOUND ATTENUATION COEFFICIENT ESTIMATION

CROSS-REFERENCE TO RELATED APPLICATIONS

This application represents the national stage entry of PCT/US2020/012325 filed on Jan. 6, 2020 and claims the benefit of U.S. Provisional Patent Application Ser. No. 62/788,430, filed on Jan. 4, 2019, and entitled "SYSTEMS AND METHODS FOR ULTRASOUND ATTENUATION COEFFICIENT ESTIMATION," the contents of which is herein incorporated by reference in its entirety.

BACKGROUND

Ultrasound attenuation coefficient estimation ("ACE") has potential for many clinical applications, including differentiating tumors and quantifying fat content in the liver. For instance, in the non-limiting example of fat content detection, the accumulation of fatty droplets in the liver can lead to steatosis, and in many cases, steatosis might progress to fibrosis, cirrhosis, liver failure, or hepatocellular carcinoma. Fat content can increase ultrasound attenuation during ultrasound propagation in the liver; therefore, the ultrasound attention coefficient can be a useful parameter to quantify liver fat. Compared with the gold standard, liver biopsy, ACE provides non-invasive and repeatable measurements, which is important for both initial screening and follow-up exams. Hence, accurate ACE has clinical utility in fatty liver detection and assessment.

Examples of ultrasound ACE methods include the spectral shift method and the reference phantom method. The spectral shift method estimates the center frequency downshift along depth. On the other hand, the reference phantom method uses a well-calibrated phantom to normalize all the system dependent effects, such as focusing, time-gain compensation ("TGC"), and diffraction, and then estimates the frequency decay rate with depth.

SUMMARY OF THE DISCLOSURE

The present disclosure addresses the aforementioned drawbacks by providing a method for estimating ultrasound attenuation coefficient data using an ultrasound system. Signal power spectrum data and noise power spectrum data are provided to the computer system. Signal-to-noise ratio (SNR) data are computed using the signal power spectrum data and the noise power spectrum data. A frequency bandwidth is estimated using the SNR data and an ultrasound depth setting is estimated using the SNR data. Ultrasound data are then acquired using the frequency bandwidth and the ultrasound depth setting, and attenuation coefficient data are estimated from the ultrasound data.

It is another aspect of the present disclosure to provide a method for generating elevational focusing normalized data using an ultrasound system. First data are acquired with an ultrasound system. The first data are acquired with a first elevational focus setting and a first lateral focus setting. Second data are acquired with the ultrasound system. The second data are acquired with the first elevational focus setting and a second lateral focus setting that is different from the first lateral focus setting. Elevational focusing normalized data are then generated by normalizing the second data using the first data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for improved ultrasound attenuation coefficient estimation ("ACE") techniques. In one aspect, noise can be suppressed by using signal-to-noise ratio ("SNR") as a quality control metric for restricting depth ranges for ACE. In this way, the proper depth range for each frequency component can be adaptively changed with sufficient SNR for ACE. In another aspect, lateral focusing reduction and elevation focusing normalization can be used to reduce errors associated with diffraction effects when estimating attenuation coefficient. In another aspect, methods for suppressing noise in ACE techniques are provided. Noise can be suppressed based on a noise field computed from measurements obtained without ultrasound transmission, based on a unique combination of consecutive image frames, based on singular value decomposition ("SVD") clutter filtering cutoff values, or combinations thereof.

In ultrasound imaging, the frequency spectrum of backscattered ultrasound signals for ACE can be modeled as the summation of the frequency spectra of pure signal and noise as, $$Y(f) = S(f) + N(f) \quad (1)$$

where $Y(f)$ is the measured frequency spectrum, $S(f)$ is the frequency spectrum of pure signal, and $N(f)$ is the noise frequency spectrum. Then, the frequency power spectrum of the backscattered signals can be calculated as, $$|Y(f)|^2 = Y(f)Y(f)^* = (S(f) + N(f))(S(f) + N(f))^* \quad (2)$$
$$= S(f)S(f)^* + N(f)N(f)^* + S(f)N(f)^* + S(f)^*N(f);$$

where * indicates the complex conjugate. Because the noise and pure signal are uncorrelated, the term $S(f)N(f)^*$ and $S(f)^*N(f)$ have zero expectations. Therefore, Eqn. (2) can be reduced to, $$|Y(f)|^2 = S(f)S(f)^* + N(f)N(f)^* = |S(f)|^2 + |N(f)|^2 \quad (3).$$

If the noise power spectrum, $|N(f)|^2$, can be measured, the pure signal power spectrum can be estimated as, $$|S(f)|^2 = |Y(f)|^2 - |N(f)|^2 \quad (4).$$

Figure 1:
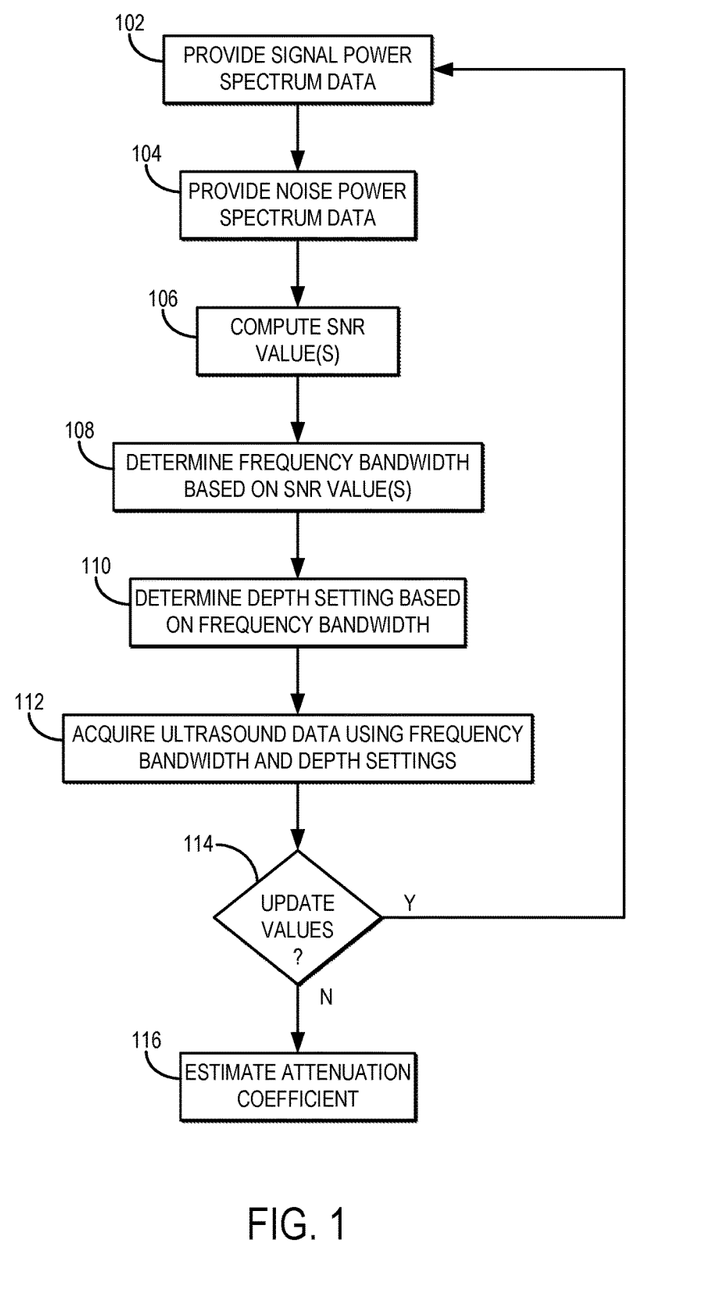
FIG. 1 is a flowchart setting forth the steps of an example method for computing SNR and using the SNR as a quality metric for adaptively restricting the depth range for frequency components in ultrasound attenuation coefficient estimation.

As noted, in some aspects of the present disclosure a method is provided for ACE in which SNR is used as a quality metric for adaptively restricting the depth range for frequency components in ACE. Referring now to FIG. 1, a flowchart is illustrated as setting forth the steps of an example method for computing SNR and using the SNR as a quality metric for adaptively restricting the depth range for frequency components in ultrasound attenuation coefficient estimation.

The method includes providing signal power spectrum data to a computer system, as indicated at step 102. The signal power spectrum data may include a measured signal power spectrum, $|Y(f)|^2$, or an estimated signal power spectrum, $|S(f)|^2$. The signal power spectrum data may be provided to the computer system by accessing or retrieving signal power spectrum data from a memory or other data storage device or medium. Additionally or alternatively, the signal power spectrum data can be acquired with an ultrasound system and provided to the computer system, which may form a part of the ultrasound system.

The method also includes providing noise power spectrum data, $|N(f)|^2$, to the computer system, as indicated at step 104. Like the signal power spectrum data, the noise power spectrum data can be provided to the computer system by accessing or retrieving signal power spectrum data from a memory or other data storage device or medium, or by acquiring the noise power spectrum data with an ultrasound system.

Using the signal power spectrum data and the noise power spectrum data, one or more SNR values are computed, as indicated at step 106. The one or more SNR values indicate the amount of noise contained in the noise power spectrum. The one or more SNR values as computed as a function of frequency. As one example, the SNR values can be computed as, $$SNR(f) = \frac{|Y(f)|^2}{|N(f)|^2} \text{ or } SNR(f) = \frac{|S(f)|^2}{|N(f)|^2}. \quad (5)$$

As another example, the SNR values can be computed as the SNR in the logarithm domain, $$SNR_{dB}(f) = 10 \log|Y(f)|^2 - 10 \log|N(f)|^2 \text{ or}$$

$$SNR_{dB}(f) = 10 \log|S(f)|^2 - 10 \log|N(f)|^2 \quad (6)$$

Using the one or more SNR values, a frequency bandwidth for a subsequent ACE technique is determined, as indicated at step 108. As an example, determining the frequency bandwidth can include computing or otherwise determining an upper and lower bound of the frequency bandwidth. For instance, thresholds can be applied to define the minimum and maximum boundaries of frequency bandwidth. As an example, the following SNR thresholds could be used, $$SNR(f) \geq 1 \text{ or } SNR_{dB}(f) \geq 0 \quad (7)$$

Using the determined frequency bandwidth, a depth setting can be determined for ACE, as indicated at step 110. For instance, the depth setting can be determined by analyzing a frequency decay curve with corresponding noise curves. As another example, the frequency bandwidth and the depth setting can be determined by analyzing an SNR map. In these instances, an SNR map (e.g., a two-dimensional SNR map) can be generated from the SNR values. This SNR map indicates SNR values as a function of frequency and depth.

Ultrasound data can then be acquired by operating an ultrasound system using the determined frequency bandwidth and depth settings, as indicated at step 112. This process can be iteratively carried out, such that the acquired ultrasound data are processed according to the methods described above in order to adaptively update the frequency bandwidth, the depth setting, or both, as indicated at decision block 114. For instance, signal power spectrum data and noise power spectrum data are provided by computing, estimating, extracting, or otherwise determining these data from the acquired ultrasound data, and these signal power spectrum data and noise power spectrum data are processed as described above to estimate new frequency bandwidth and depth setting parameters. Ultrasound attenuation coefficients can then be estimated from the acquired ultrasound data, as indicated at step 116. Using the estimated attenuation coefficients, one or more attenuation coefficient maps can be generated to display to a user, to store for later use or processing, or both.

Figure 2:
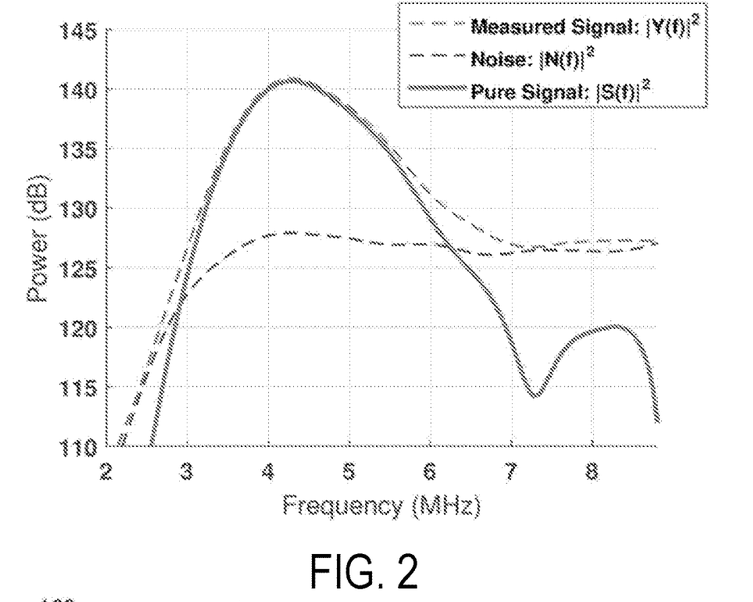
FIG. 2 is an example of power spectra of backscattered signals (red dashed curve) and noise (blue dashed curve) in a base-10 logarithm domain.

An example of signal power spectrum data and noise power spectrum data is shown in FIG. 2. Specifically, FIG. 2 shows power spectra of backscattered signals (red dashed curve) and noise (blue dashed curve) in a base-10 logarithm domain measured at 6 cm depth. The red solid curve shows the pure signal power spectra in the base-10 logarithm domain. In the example shown in FIG. 2, the SNR thresholds in Eqn. (7) can be used to define a frequency bandwidth approximately from 3-7 MHz for a measured signal power spectrum, $|Y(f)|^2$, and a frequency bandwidth of 3-6 MHz for an estimated signal power spectrum, $|S(f)|^2$.

Figure 3:
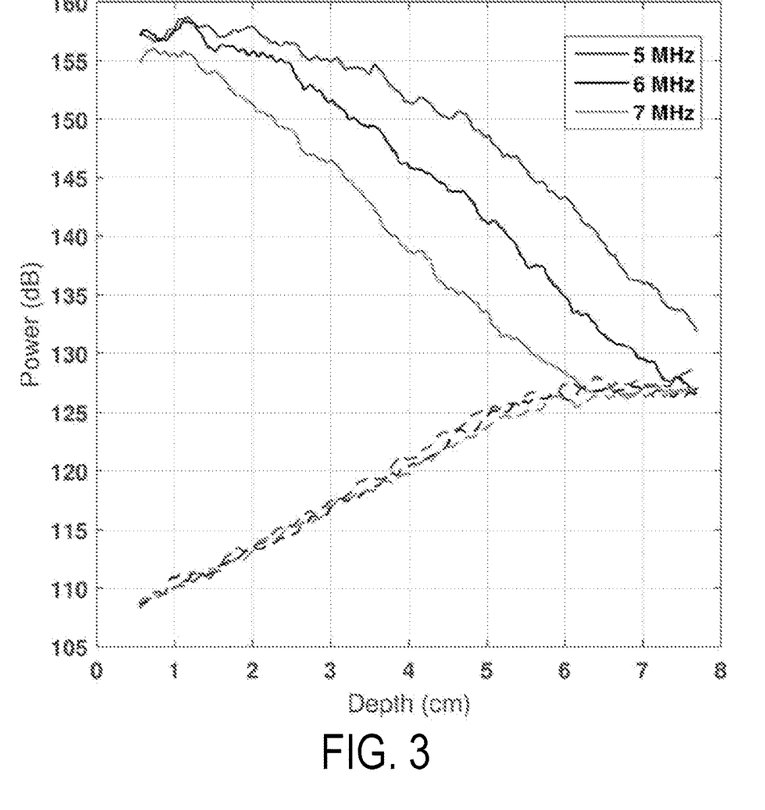
FIG. 3 is an example of measured frequency power decay curves (solid curves) along depth at three example frequencies (i.e., 5 MHz, 6 MHz, and 7 MHz). The corresponding noise power changes with depth are shown in dashed curves.

In practice, the measured ultrasound signal power spectra usually change along depth. FIG. 3 shows an example of measured frequency power decays along depth at three example frequencies: 5 MHz, 6 MHz, and 7 MHz. In addition, the corresponding noise power changes with depth are also shown in dashed curves. The noise power increases with depth because of time gain compensation. From FIG. 3, by comparing the frequency decay curves with their corresponding noise curves, the frequency-and-depth-dependent SNR can be calculated at each frequency and each depth. Therefore, the SNR can also be used to adaptively restrict a proper depth range for each frequency component with sufficient SNR for ACE.

In the example of FIG. 3 and using the SNR thresholds in Eqn. (7), the following depth ranges can be relied upon for ACE. For 5 MHz, the whole depth region in the figure can be used for ACE. For 6 MHz, an ACE depth range can be selected approximately from 0.5 cm to 7 cm. And for 7 MHz, an ACE depth range can be selected approximately from 0.5 cm to 6 cm.

Figure 4:
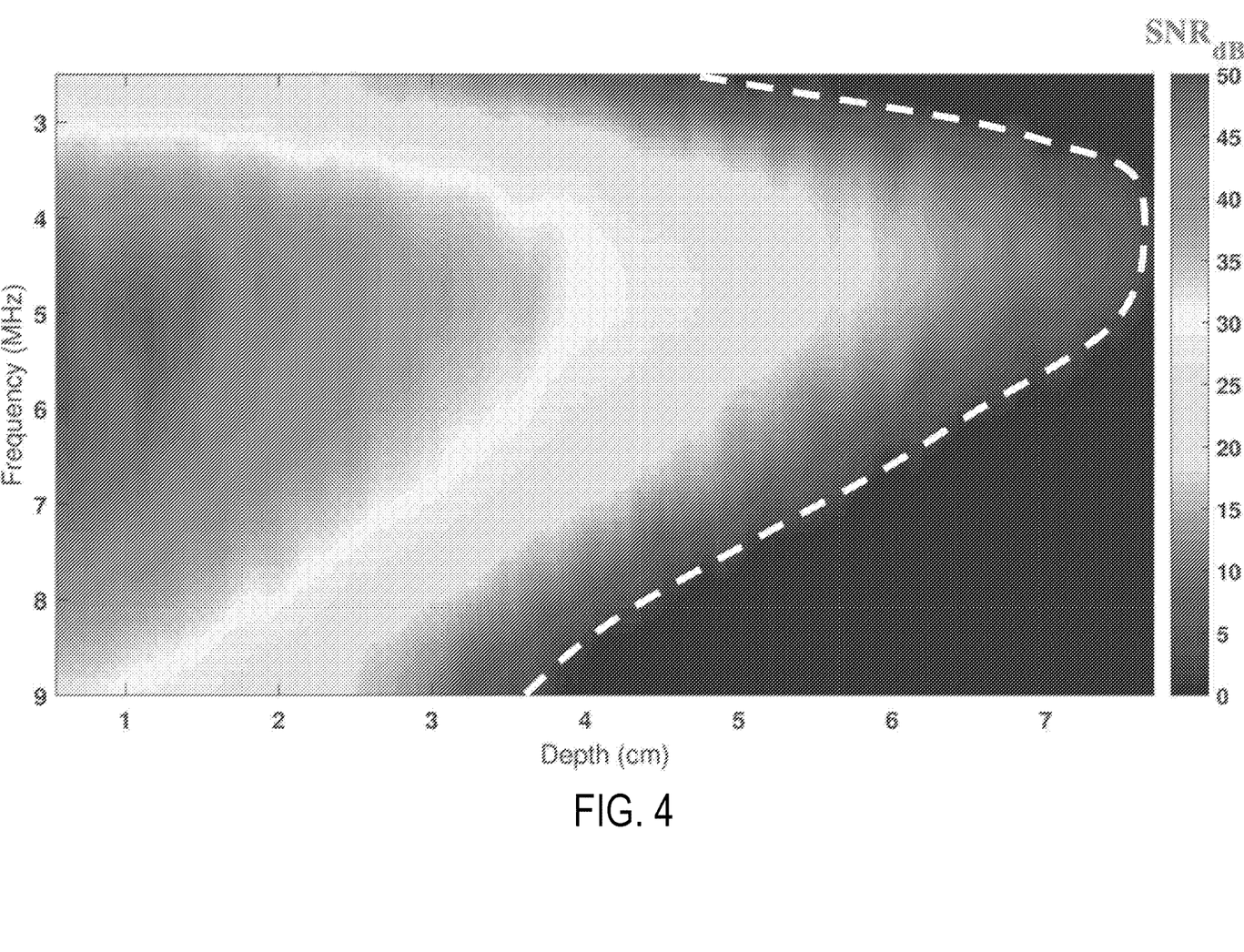
FIG. 4 is an example of a 2D SNR map in the logarithm domain as a function of frequency (y-axis) and depth (x-axis). The white dashed curve indicates the regions where SNR is greater than zero.

FIG. 4 shows an example of a two-dimensional map of the frequency-and-depth-dependent SNR in the logarithm domain. In this example, the y-axis is frequency, f, and the x-axis is depth, z. As described above, the SNR can be used to determine the effective depth range at each frequency or to determine the effective frequency bandwidth at certain depth or to determine both simultaneously for ACE. As one non-limiting example, the frequency bandwidth and depth region for more reliable ACE can be selected as the region where SNR is greater than zero as labelled by the white dashed curve in FIG. 4.

As noted, in some aspects of the present disclosure a method is provided for ACE in which elevation focusing normalization is used to reduce diffraction effects that could otherwise reduce ACE accuracy. In some ultrasound ACE methods, it may be possible to normalize data from two close frequencies by taking the power ratio between these two frequencies. This normalization can be performed with an assumption that the diffraction effects at these two close frequencies are equal. This assumption is not accurate in all instances, however. For instance, this assumption is not accurate for applications with strong focusing and large f-numbers.

More generally, the beam diffraction patterns may change rapidly along depth at different frequencies and cannot be completely cancelled. In these instances, the residual diffraction effects can affect the ACE accuracy. As one example, this challenge can be addressed by placing the focus location outside the depth range. Generally, the lateral focus can also be adjusted to realize this solution. As another example, multiple ultrasound image frames can be acquired with lateral focuses set at different depth locations. Then, the multiple ultrasound frames can be averaged or the power spectra acquired from these frames can be averaged to reduce the lateral focusing effect. However, the elevational focus is usually fixed for many clinical transducers, which makes the depth range selection inflexible in these systems. Thus, the systems and methods described in the present disclosure can provide an effective way to normalize the non-adjustable elevation focusing effect for more flexible depth range selection for ACE.

Figure 5:
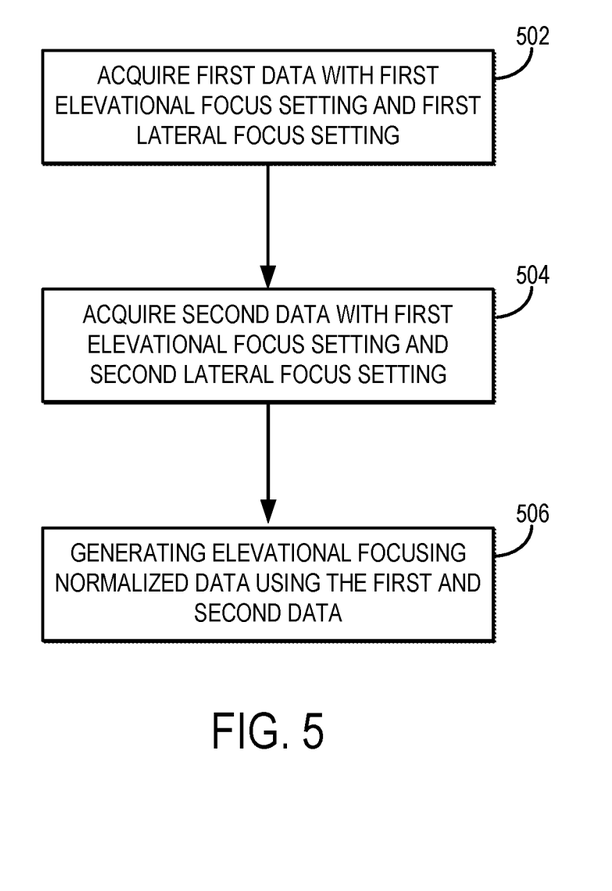
FIG. 5 is a flowchart setting forth the steps of an example method for elevation focusing normalization.

Referring now to FIG. 5, a flowchart is illustrated as setting forth the steps of an example method for elevation focusing normalization. The method includes acquiring first ultrasound data, as indicated at step 502. The first ultrasound data may be, for example, a first frame of B-mode data. In particular, the first ultrasound data are acquired with a lateral focus that coincides with the elevation focus. Additionally, the first ultrasound data should be acquired using the same lateral f-number and elevational f-number. Taking as an example a lateral focus and an elevational focus set at 6 cm, it can be assumed that $$D_{elev}=D_{lat,6cm} \quad (8);$$

where $D_{elev}$ and $D_{lat,6cm}$ are the diffraction patterns of the elevational focusing and lateral focusing at 6 cm, respectively. The diffraction pattern is a function of both frequency, f, and depth, z. The total diffraction pattern in the backscattered power spectrum is the multiplication of the two focusing effects, and can be expressed as, $$D_{Total\_1}=D_{elev}D_{lat,6cm}=D_{elev}^2 \quad (9).$$

The method also includes acquiring second ultrasound data, as indicated at step 504. The second ultrasound data may be, for example, a second frame of B-mode data. In particular, the second ultrasound data are acquired using the same transducer and acquisition parameter settings as the first ultrasound data except that a different lateral focus location is set for the second ultrasound data. In general, the lateral focus of the second frame can be set outside the ACE depth range for reduced diffraction impact. For example, for an ACE depth range from 5-8 cm depth, a lateral focus at 4 cm depth can be used. Thus, in some instances, the ACE depth range can be selected using the methods described above and then used to select the acquisition parameters for the second ultrasound data here. The total diffraction for the second ultrasound data is, $$D_{total\_2}=D_{elev}D_{lat,4cm} \quad (10)$$

In practice, the first ultrasound data and the second ultrasound data can be acquired in any order (i.e., the first ultrasound data do not need to be acquired before the second ultrasound data). The elevational focusing effect can then be normalized, as indicated at step 506. For instance, the elevational focusing effect can be normalized as, $$D_{nor} = \frac{D_{Total\_2}^2}{D_{Total\_1}} = \frac{(D_{elev}D_{lat,4cm})^2}{D_{elev}^2} = D_{lat,4cm}^2. \quad (11)$$

Using this normalization, the diffraction pattern has a squared lateral focusing effect at the depth outside of the depth range (e.g., 4 cm in this example), and the elevational focusing effect is cancelled. Because the lateral focus is outside the ACE depth range, its influence on the ACE accuracy is minimal. It will be appreciated to those skilled in the art that the elevational focusing normalization can be applicable to application other than ACE, such as other tissue property estimations including backscattered coefficient, effective scatterer diameter, and effective acoustic concentration.

In addition to the methods described above, the bias due to noise that contaminates the signals for ACE can be reduced. Such methods can be referred to as "noise suppression" or "noise reduction." Described here are some example methods for effectively measuring and suppressing noise from backscattered signal power spectrum data for more accurate ACE.

As one example, the noise field can be experimentally measured by turning off the transducer transmission and receiving with the same ultrasound system configuration as for the ACE signal acquisition. This method directly measures the noise floor from the ultrasound system as an estimation of the noise bias. The noise power spectrum can then be subtracted from the backscattered signal power spectrum to obtain the pure signal power spectrum using Eqn. (4). FIG. 2 shows an example of measured signal and noise power spectra in the logarithm domain (red dashed curve: measured signal; blue dashed curve: measured noise). Then, the pure signal power spectrum, $|S(f)|^2$ can be generated by subtracting the noise power from the backscattered signal power at each frequency in the spectrum, as in Eqn. (4). The red sold curve shows the pure signal power spectrum after noise reduction in the logarithm domain. The noise influence on the ACE power spectrum is effectively suppressed.

As another example, the noise bias can be measured by acquiring two frames of ultrasound B-mode data consecutively as, $$Y_1(f)=S_1(f)+N_1(f) \quad (12);$$

$$Y_2(f)=S_2(f)+N_2(f) \quad (13).$$

If the interleaved time interval between the two ultrasound frames is minimized and the imaging object is relatively stationary, then it can be assumed that $S_1(f)=S_2(f)$. The summation of Eqns. (12) and (13) then gives, $$Y_1(f)+Y_2(f)=2S(f)+N_1(f)+N_2(f) \quad (14);$$

and the subtraction of Eqns. (12) and (13) gives, $$Y_1(f)-Y_2(f)=N_1(f)-N_2(f) \quad (15).$$

The power spectra of Eqns. (14) and (15) can be calculated as, $$|Y_1(f)+Y_2(f)|^2=4|S(f)|^2+|N_1(f)|^2+|N_2(f)|^2=4|S(f)|^2+2|N(f)|^2 \quad (16);$$

and $$|Y_1(f)-Y_2(f)|^2=|N_1(f)|^2+|-N_2(f)|^2=2|N(f)|^2 \quad (17)$$

Eqns. (16) and (17) contain the same amount of noise power, and so the pure signal power spectrum can be estimated as, $$|s(f)|^2=\tfrac{1}{4}(|Y_1(f)+Y_2(f)|^2-|Y_1(f)-Y_2(f)|^2) \quad (18)$$

Figure 6:
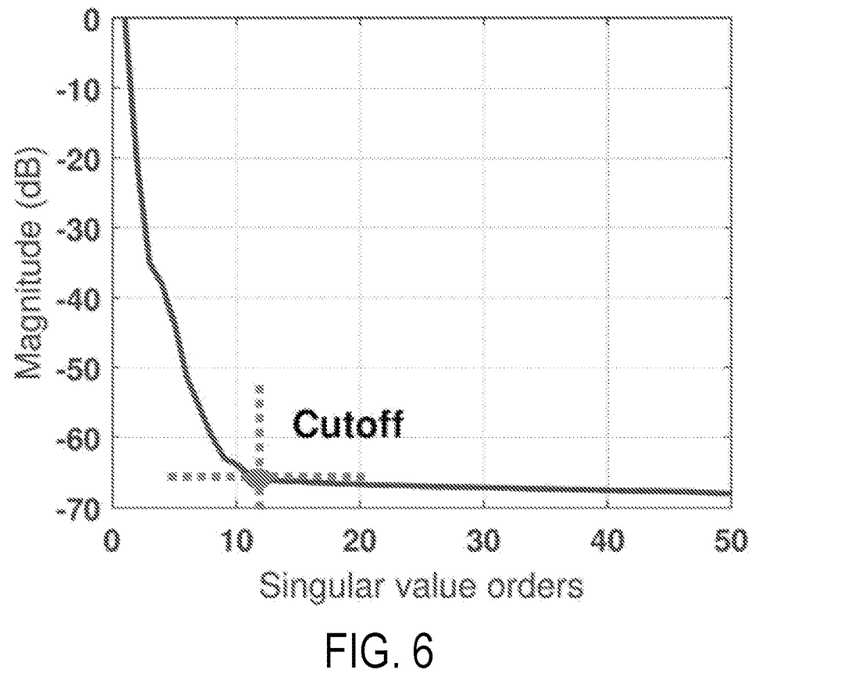
FIG. 6 is an example of a singular value distribution after acquiring 50 frames of B-mode images. The red dot indicates one non-limiting example of cutoff order selection.

As still another example, clutter filters such as those used in ultrasound Doppler imaging (e.g., singular value decomposition ("SVD") clutter filters) can be applied to suppress the noise in ACE. For example, multiple B-mode images can be obtained consecutively for SVD processing. FIG. 6 shows an example of a singular value distribution after acquiring 50 frames of B-mode images. In general, the high-order singular values mainly correspond to noise.

Figure 7:
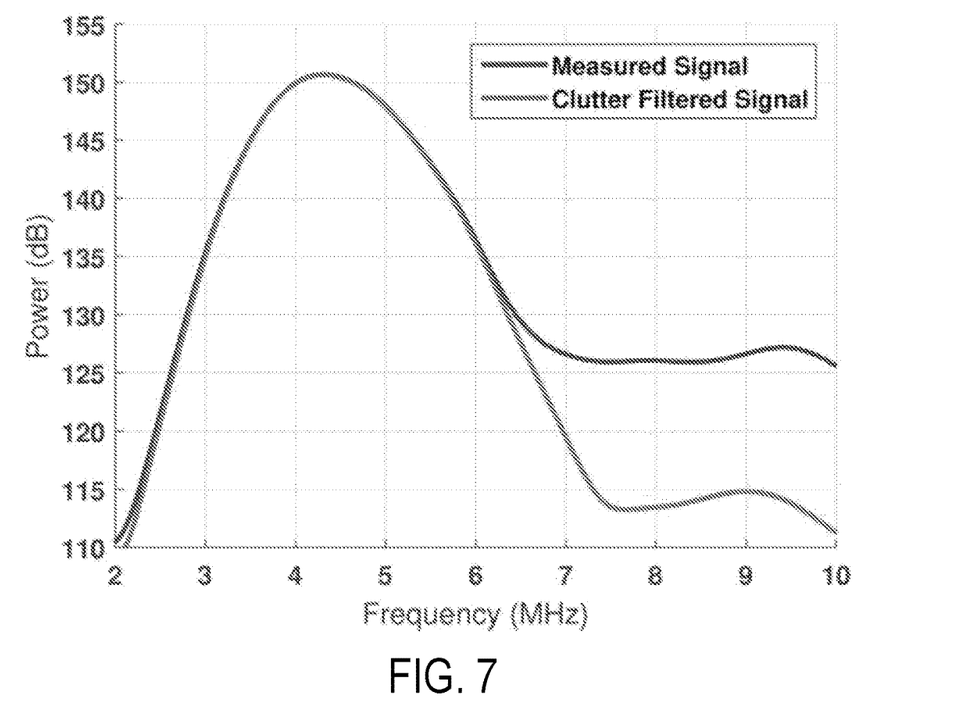
FIG. 7 is an example power spectra of backscattered signals without (blue curve) and with (red curve) an SVD clutter filter.

A cutoff order (red dot in FIG. 6) can be selected to filter out the signals corresponding to the singular value orders that above a given cutoff before the ACE analysis. FIG. 7 shows an example of the power spectra of the backscattered signals without (blue curve) and with (red curve) the SVD clutter filter. The noise in the measured ACE power spectrum has been suppressed by the clutter filter. An example of SVD clutter filtering is described in co-pending International Patent Application No. PCT/US2017/016190, which is herein incorporated by reference in its entirety.

Figure 8:
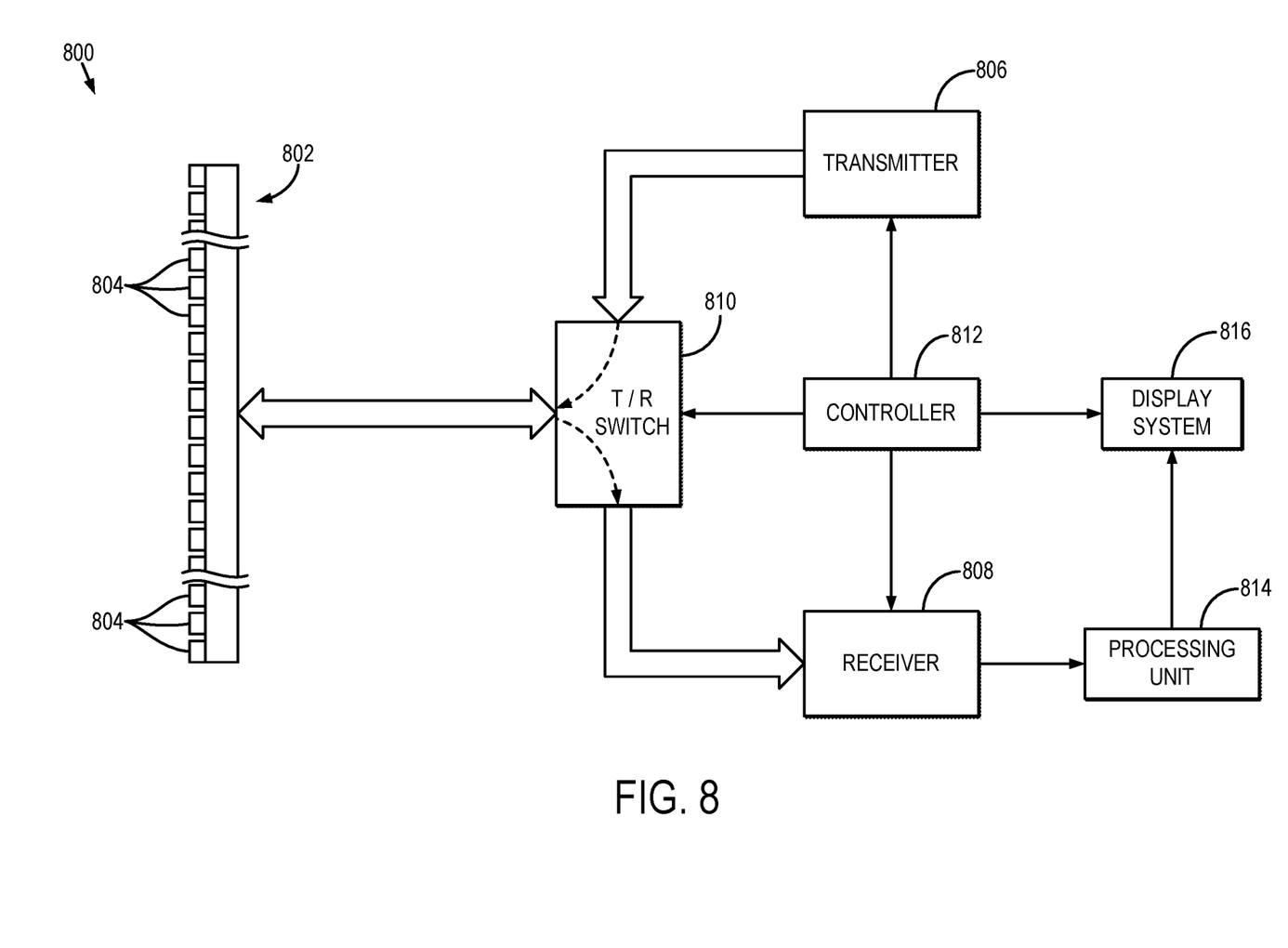
FIG. 8 is a block diagram of an example ultrasound system that can implement the methods described in the present disclosure.

Another example of "noise" is the speckle noise due to constructive and destruction interferences from the backscattered signals. The speckle noise results in oscillations on the normalized frequency spectra, which undermines ACE accuracy. To improve estimation accuracy in ACE, speckle noise effects can be reduced by averaging the power spectra from multiple A-lines. In one example, the A-lines can be selected laterally within a relatively uniform region from one ultrasound frame. In another example, multiple ultrasound frames corresponding to different regions (and thus different scatterers) can be acquired when the target anatomy (e.g., the liver) moves during a patient's free breathing. Then, A-line averaging can be performed using A-lines from different lateral locations within the same frame, or from different ultrasound frames, or both FIG. 8 illustrates an example of an ultrasound system 800 that can implement the methods described in the present disclosure. The ultrasound system 800 includes a transducer array 802 that includes a plurality of separately driven transducer elements 804. The transducer array 802 can include any suitable ultrasound transducer array, including linear arrays, curved arrays, phased arrays, and so on. Similarly, the transducer array 802 can include a 1 D transducer, a 1.5 D transducer, a 1.75 D transducer, a 2 D transducer, a 3 D transducer, and so on.

When energized by a transmitter 806, a given transducer element 804 produces a burst of ultrasonic energy. The ultrasonic energy reflected back to the transducer array 802 (e.g., an echo) from the object or subject under study is converted to an electrical signal (e.g., an echo signal) by each transducer element 804 and can be applied separately to a receiver 808 through a set of switches 810. The transmitter 806, receiver 808, and switches 810 are operated under the control of a controller 812, which may include one or more processors. As one example, the controller 812 can include a computer system.

The transmitter 806 can be programmed to transmit unfocused or focused ultrasound waves. In some configurations, the transmitter 806 can also be programmed to transmit diverged waves, spherical waves, cylindrical waves, plane waves, or combinations thereof. Furthermore, the transmitter 806 can be programmed to transmit spatially or temporally encoded pulses.

The receiver 808 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 806 and the receiver 808 can be programmed to implement a high frame rate. For instance, a frame rate associated with an acquisition pulse repetition frequency ("PRF") of at least 100 Hz can be implemented. In some configurations, the ultrasound system 800 can sample and store at least one hundred ensembles of echo signals in the temporal direction.

The controller 812 can be programmed to design an acquisition sequence using the techniques described in the present disclosure, or as otherwise known in the art. In some embodiments, the controller 812 receives user inputs defining various factors used in the design of the acquisition sequence. In some examples, ultrasound data can be acquired using a plane wave ultrasound acquisition. In other examples, ultrasound data can be acquired using an acquisition scheme that implements one or more focused ultrasound beams. Still other examples for acquiring ultrasound data can be used according to the knowledge of those skilled in the art.

A scan can be performed by setting the switches 810 to their transmit position, thereby directing the transmitter 806 to be turned on momentarily to energize transducer elements 804 during a single transmission event according to the designed acquisition sequence. The switches 810 can then be set to their receive position and the subsequent echo signals produced by the transducer elements 804 in response to one or more detected echoes are measured and applied to the receiver 808. The separate echo signals from the transducer elements 804 can be combined in the receiver 808 to produce a single echo signal.

The echo signals are communicated to a processing unit 814, which may be implemented by a hardware processor and memory, to process echo signals or images generated from echo signals. As an example, the processing unit 814 can acquire ultrasound data using acquisition parameters (e.g., frequency bandwidth and depth) that are determined using the methods described in the present disclosure. As another example, the processing unit 814 can estimate attenuation coefficient values and generate attenuation coefficient maps from data acquired using the methods described in the present disclosure. As another example, the processing unit 814 can generate elevational focusing normalized data using the methods described in the present disclosure. The processing unit 814 can also generate noise reduced or noise suppressed data using the methods described in the present disclosure. Images produced from the echo signals by the processing unit 814 can be displayed on a display system 816.

The present disclosure has described one or more preferred embodiments, and it should be appreciated that many equivalents, alternatives, variations, and modifications, aside from those expressly stated, are possible and within the scope of the invention.

The invention claimed is:

1. A method for estimating ultrasound attenuation coefficient data using an ultrasound system, the steps of the method comprising:
   (a) providing signal power spectrum data to a computer system;
   (b) providing noise power spectrum data to the computer system;
   (c) computing signal-to-noise ratio (SNR) data using the signal power spectrum data and the noise power spectrum data;
   (d) estimating at least one of a frequency bandwidth using the SNR data or an ultrasound depth setting using the SNR data;
   (e) acquiring ultrasound data from a subject with the ultrasound system by controlling the ultrasound system to perform an acquisition scheme using the at least one of the frequency bandwidth or the ultrasound depth setting;
   (f) generating a backscattered signal power spectrum data from the acquired ultrasound data;
   (g) generating pure signal power spectrum data by subtracting the noise power spectrum data from the backscattered signal power spectrum data; and
   (h) estimating attenuation coefficient data using the pure signal spectrum data from the ultrasound data acquired with the ultrasound system, wherein noise in the attenuation coefficient data is suppressed based on using the at least one of the frequency bandwidth or the ultrasound depth setting when acquiring the ultrasound data, wherein the noise in the attenuation coefficient data is additionally suppressed by using the pure signal spectrum data in the attenuation coefficient data estimation.

2. The method as recited in claim 1, wherein estimating the frequency bandwidth comprises estimating an upper bound of the frequency bandwidth and estimating a lower bound of the frequency bandwidth based on the SNR data.

3. The method as recited in claim 1, wherein the ultrasound depth setting is estimated by analyzing a frequency decay curve as a function of the SNR data.

4. The method as recited in claim 1, wherein step (d) comprises estimating both the frequency bandwidth and the ultrasound depth setting by generating an SNR map from the SNR data and processing the SNR map to select the frequency bandwidth and the ultrasound depth setting.

5. The method as recited in claim 1, wherein the signal power spectrum data comprise measured signal power spectrum data.

6. The method as recited in claim 1, wherein the signal power spectrum data comprise estimated signal power spectrum data.

7. The method as recited in claim 1, wherein the attenuation coefficient data comprise an attenuation coefficient map that visually depicts a spatial distribution of attenuation coefficient values in a region from which the ultrasound data were acquired.

8. The method as recited in claim 2, wherein the upper bound of the frequency bandwidth and the lower bound of the frequency bandwidth are estimated based on thresholding the SNR data with at least one threshold value.

9. The method as recited in claim 8, wherein the at least one threshold value comprises a first threshold value and a second threshold value and wherein the upper bound of the frequency bandwidth is estimated based on thresholding the SNR data with the first threshold value and the lower bound of the frequency bandwidth is estimated based on thresholding the SNR data with the second threshold value.

10. A method for estimating ultrasound attenuation coefficient data using an ultrasound system, the steps of the method comprising:
   (a) providing signal power spectrum data to a computer system;
   (b) providing noise power spectrum data to the computer system;
   (c) computing signal-to-noise ratio (SNR) data using the signal power spectrum data and the noise power spectrum data;
   (d) estimating at least one of a frequency bandwidth using the SNR data or an ultrasound depth setting using the SNR data;
   (e) acquiring ultrasound data from a subject with the ultrasound system by controlling the ultrasound system to perform an acquisition scheme using the at least one of the frequency bandwidth or the ultrasound depth setting;
   (f) updating the at least one of the frequency bandwidth or the ultrasound depth setting after acquiring the ultrasound data by estimating updated signal power spectrum data and updated noise power spectrum data from the acquired ultrasound data and repeating steps (c)-(d) using these estimated updated signal power spectrum data and updated noise power spectrum data to estimate the at least one of the updated frequency bandwidth or the updated ultrasound depth setting;
   (g) acquiring updated ultrasound data using the at least one of the updated frequency bandwidth or the updated ultrasound depth setting;
   (h) generating a backscattered signal power spectrum data from the updated ultrasound data;
   (i) generating pure signal power spectrum data by subtracting the updated noise power spectrum data from the backscattered signal power spectrum data; and
   (j) estimating attenuation coefficient data using the pure signal spectrum data, wherein noise in the attenuation coefficient data is suppressed based on using the at least one of the updated frequency bandwidth or the updated ultrasound depth setting when acquiring the updated ultrasound data, wherein the noise in the attenuation coefficient data is additionally suppressed by using the pure signal spectrum data in the attenuation coefficient data estimation.

* * * * *